United States Patent
Seguin

(10) Patent No.: US 8,623,338 B2
(45) Date of Patent: Jan. 7, 2014

(54) METHIONINE-DERIVED PEPTIDOMIMETICS AND THEIR USE IN THE PROTECTION OF MITOCHONDRIA OF CUTANEOUS CELLS

(75) Inventor: Marie-Christine Seguin, Monaco (MC)

(73) Assignee: Exsymol S.A.M., Monaco (MC)

( * ) Notice: Subject to any disclaimer, the term of this patent is extended or adjusted under 35 U.S.C. 154(b) by 62 days.

(21) Appl. No.: 13/234,730

(22) Filed: Sep. 16, 2011

(65) Prior Publication Data

US 2012/0070394 A1   Mar. 22, 2012

(30) Foreign Application Priority Data

Sep. 17, 2010  (FR) .................................... 10 03708

(51) Int. Cl.
*A61K 8/00*   (2006.01)
*A61K 31/16*   (2006.01)
*C07C 381/00*   (2006.01)

(52) U.S. Cl.
USPC ............ 424/62; 514/616; 564/154; 977/788; 977/906

(58) Field of Classification Search
USPC ............ 424/62; 514/616; 564/154; 977/788, 977/906
See application file for complete search history.

(56) References Cited

U.S. PATENT DOCUMENTS

| 4,956,173 A | 9/1990 | Le Fur et al. |
| 2009/0234011 A1 | 9/2009 | Goldstein |

FOREIGN PATENT DOCUMENTS

| EP | 0318393 A1 | 5/1989 |
| WO | 2006/116353 A2 | 11/2006 |

OTHER PUBLICATIONS

Picciola, G et al., "Derivati Della Metionina Ad Attivita Epatoprotettrice", Farmaco, Edizione Scientifica, Societa Chmca ta ana, Pava, t, Jan. 1986, pp. 758-780, Vo.41.*

Naider et al., "Synthesis and Optical Studies of L-Methionine Oligopeptides un Solution," in Biopolymers, vol. 13, 1011-1022 (1974).*

Ribeiro et al., "The Preferred Conformations of Protected Homodi- To Homoheptamethionine Peptides" IN International Journal of Peptide and Protein Research, 1979, 14(5), 414-436.*

Picciola, G et al., "Derivati Della Metionina Ad Attivita Epatoprotettrice", Farmaco, Edizione Scientifica, Societa Chimica Italiana, Pavia, It, Jan. 1986, pp. 758-780, vol. 41, cited in FSR.

French Search Report (FSR) of French Appl No. 1003708, dated Jun. 8, 2011.

* cited by examiner

*Primary Examiner* — Blessing M Fubara
(74) *Attorney, Agent, or Firm* — Westerman, Hattori, Daniels & Adrian, LLP

(57) ABSTRACT

The invention concerns a methionine-derived peptidomimetic represented by the following general formula (II):

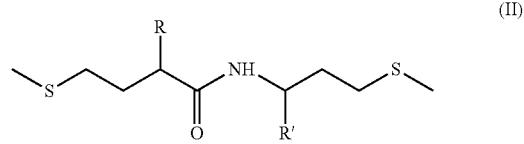

R=X—C(O)—NH— with X=alkyl or alkyloxy ($C_1$-$C_4$); R'=H

The invention also concerns a composition for preventing or fighting cutaneous disorders associated to a mitochondrial dysfunction, and the use of a methionine-derived peptidomimetic as a cosmetic agent for protecting and/or stimulating the mitochondria of cutaneous cells.

8 Claims, No Drawings

METHIONINE-DERIVED PEPTIDOMIMETICS AND THEIR USE IN THE PROTECTION OF MITOCHONDRIA OF CUTANEOUS CELLS

FIELD OF THE INVENTION

The invention concerns a selection of peptidomimetics derived from methionine aminoacid, and their use as protective agent of mitochondria of cutaneous cells. The invention also concerns compositions intended for preventing or fighting against the cutaneous disorders associated to a mitochondrial dysfunction.

BACKGROUND OF THE INVENTION

Cytoplasmic organelle present in the plant and animal cells, the mitochondria plays a primordial role for these cells. Indeed, mitochondria are announced to be << the energetic power stations of our cells >> with the production and the storage of adenosine triphosphate (ATP), universal energetic component necessary to any eukaryote cell functioning.

The comburent, necessary for such a production via a cluster of redox chemical reactions commonly called "the mitochondrial respiratory chain", is oxygen. Oxygen is thus essential to the cell functioning, but paradoxically, it is also the initial and parallel source of reactive species called "oxygen-derived reactive species" (ERO in French, ROS in English) which are potentially toxic for cell biochemical macromolecules (DNA, proteins, lipids, etc.).

In order to neutralize this ROS formation, any cell naturally develop some antioxidant defense systems, enzymatic or not, requiring some energy to operate, which is in the first place precisely this ATP issued from the mitochondrial respiratory chain (Singh K. K., FEMS Yeast Res., 2004, vol. 5, pp. 127-132). But when an imbalance between ROS production and removal by intracellular defense systems emerges as ROS amounts become too intense, the resulting oxidant stress thus generates gradually a decline of mitochondrial functions, notably expressed by a disruption of the energy-producer electrons' flux and by a ROS formation within the mitochondria, called "intra-mitochondrial ROS" (Jones D. P., Chemico Biological Comm., 2006, vol. 163, pp. 38-53). Such an imbalance and energy deficiency at the cell level compromise its ability to adapt to physiological stress to which it is exposed. This in fine contributes to the cell aging phenomenon (Trifunovic A. and al., J. of Internal Medicine, vol. 263, pp. 167-178). It is also admitted that these disruptions originating from mitochondria are clearly involved with the genesis of a large spectrum of pathologies or tissue disorders (Barlow-Stewart K., The Australasian Genetics Ressource Book, 2007, pp. 1-3 and quoted references).

Source of intracellular ROS, mitochondria remains the main target. Consequently and in order to preserve at best the functional and/or structural integrity of any mitochondria, one of the current concerns of many researchers is to reduce the oxidative metabolism originating from mitochondria and to stimulate or to protect the mitochondria functions.

In the state of the art displayed these last years with same objectives, retained strategies and systems are often shared among:

the selection of powerful antioxidants that carry one or several thiol or phenol moieties, and that are found at the natural state in the animal or plant kingdoms, like thioctic acid better known as alpha-lipoic acid with evidenced benefits against the mitochondrial aging (Palaniappan A. R. and al., Neurochem. Res., 2007, vol. 32, pp. 1552-8), or else ergothionein that is a thiourea derivative announced to protect the mitochondria membranes of mammals (U.S. Pat. No. 6,479,533), the use of some molecules or conventional antioxidant proteins, however modified by the addition/grafting of groups or sequences (hydrophobic cation, etc.) with a strong affinity for mitochondria and for a greater inner storage (Kagan V. E. and al., Adv. Drug Delivery Rev., 2009, vol. 61, pp. 1375-85), the development of small peptides announced "cell-permeable" that alternate some basic and aromatic aminoacid residues, due to their ability to penetrate the mitochondrial inner membrane and then to express within it some properties of cyto- and mitoprotection (Szeto H. H., Antioxidants & Redox Signaling, 2008, vol. 3, pp. 1-15).

SUMMARY OF THE INVENTION

The present invention has been developed in a same context of identification of new products or new preparations in order to respond to the general requirement with << to improve the functioning of the mitochondria >> (B. Lacroix, Nutranews, April 2008), however with cosmetic and/or dermatological applications due to mainly the cutaneous topical administration of these products or preparations and with the following concomitant objectives:

to preserve/restore an efficient metabolic activity of mitochondria of skin cells when the latter are physiologically affected;

to display an acceptable bioavailability in the deep layers of skin. On the one hand, it is admitted that it is an essential prerequisite for an in vivo mitochondria protection of cutaneous cells. On the other hand, it is useful to avoid a premature metabolization in the superior layers of skin even before to be able to act on the epidermic and dermic cells;

to oppose the deleterious effects of oxygen-derived reactive species on these same cells, as well as ROS with intra-mitochondrial formation than with extracellular origin (ultra-violet radiations, pollution, oxidative environmental toxins, etc.).

In order to reach these objectives, the applicant investigated towards thioether compounds for which it is assigned an ability to deactivate ("quenching") various excited states of oxygen such as for instance $O_2^{\circ-}$ and $^1O_2$ (Cohen S. G. and L., J. Am. Chem. Soc., 1975, vol. 97, pp. 5633-5634 and quoted references).

The applicant is more especially interested in methionine sulfur alpha-amino acid in which the sulfur atom participates in a same thioether function (S—CH$_3$), this in spite of some methionine-attached characteristics contrary to the desired aims a smell of thioorganic derivatives that is little suitable for cosmetic/dermatological use, a low penetration power in the skin, and above all the evidence of intra-mitochondrial ROS and of mitochondrial DNA oxidative damages generated by a diet supplementation in methionine (Caro P. and al., Rev. Esp. Geriatr. Gerontol., 2009, vol. 44, pp. 194-199; Sanz A. and al., FASEB J., 2006, vol. 20, pp. 1064-1073). In addition, it is anticipated that the oligomethionine-type peptides (dimethionine, trimethionine, etc) sensitivity to cutaneous proteases is too high.

It is why ultimately the applicant has then directed its research towards the synthesis of methionine-derived peptidomimetics.

Thus, further to a structure-activity research, the applicant's choice stopped on a limited panel of original compounds derived from methionine, with regard to their advantageous response to the combination of above-mentioned criteria and without the drawbacks displayed by methionine or oligomethionines. This advantageous response is illustrated by:

- an excellent ability to maintain a metabolic activity of cutaneous cells exposed to a stress, reflected by a preservation of ATP level production [see test 1 below];
- a cutaneous absorption absolutely favorable, even going beyond the stratum corneum, revealed by a logarithmic value of its permeability coefficient ("Log Kp") similar to that obtained for permeant compounds such as caffeine [see test 2 below];
- an ability to reduce the mitochondrial oxidative stress, as well as an ability to modulate the mitochondrial mass (called "mitochondrial biogenesis") occurring in response to identical stress conditions [see test 3 below];
- a high cytoprotection, expressed in particular on a V79 fibroblast cell line [see test 4 below] with the characteristic that is to be sensitive to hydrogen peroxide $H_2O_2$ at the origin of disorders in the mitochondrial respiratory chain (Tatsumi T. and al., Basic Res. Cardiol., 1993, vol. 88, pp. 199-211);
- a strong antioxidant profile expressed by a scavenging ability of oxidative species (hydroxyl radical $OH°$, peroxynitrite ions $ONOO^-$, oxygen singulet $^1O_2$) that are known to affect mitochondria, ability similar to that one of reference antioxidants such as ascorbic acid or Trolox™ [see tests 5 and 6 below];
- a weak smell released by these methionine derivatives.

MODE(S) FOR CARRYING OUT THE INVENTION

The invention has therefore for first object a family of methionine-derived peptidomimetic, characterized in that it is represented by the following general formula (I):

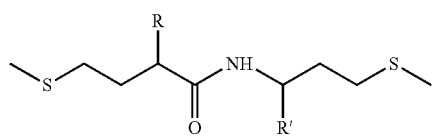

(I)

R=X—C(O)—NH— with X=alkyl or alkyloxy ($C_1$-$C_8$); R'=H

OR

R'=—C(O)—OX with X=alkyl ($C_1$-$C_8$); R=H

According to a preferred embodiment of the invention, the formula (I) is limited to the hereafter formula (II) where the radical R' is exclusively a hydrogen atom and R is a radical where X is of alkyl or alkyloxy-type with a linear or branched hydrocarbonated chain length comprising between one and four carbon atoms ($C_1$-$C_4$):

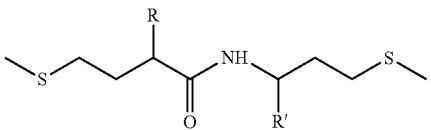

(II)

R=X—C(O)—NH— with X=alkyl or alkyloxy ($C_1$-$C_4$); R'=H

More advantageously, X in the above-mentioned formula (II) is of alkyl-type with a linear or branched hydrocarbonated chain length comprising between one and four carbon atoms ($C_1$-$C_4$).

As non limitative examples of compounds with formula (II), one can especially mention the following compounds:
—N-acetyl-(DL)-methionyl-4-(methylthio)propylamine
—N-propionyl-(DL)-methionyl-4-(methylthio)propylamine
—N-pentanoyl-(DL)-methionyl-4-(methylthio)propylamine
—N-t-butyloxy-(DL)-methionyl-4-(methylthio)propylamine According to an even more advantageous embodiment of the invention, the above-mentioned formulas (I) and (II) specifically target the N-acetyl-(DL)-methionyl-4-(methylthio)propylamine compound (R=$CH_3$—C(O)—NH— and R'=H).

According to a second aspect, the invention also covers a composition, preferably for cosmetic or dermatological use, intended for preventing or fighting against the cutaneous disorders associated to a mitochondrial dysfunction, comprising in association with any physiologically compatible additive, as main active ingredient, a methionine-derived peptidomimetic with general formula (I) such as previously defined.

In the course of the present invention, it is understood that "main active ingredient" is an active substance able to limit the functional or structural alterations of skin cell mitochondria submitted to a physico-chemical or environmental stress, by a reinforced process of mitochondria protection and/or of stimulation of some of their essential functions such as the energetic cell metabolism.

Particularly, said composition is intended for protecting skin from a stress induced by ultra-violet radiations (UV-induced stress), and the methionine derivative is of formula (II). It is more specifically the N-acetyl-(DL)-methionyl-4-(methylthio)propylamine compound.

Advantageously, the quantity of said derivative of general formula (I) in the here-above composition is comprised between 0.1 and 10% in weight in relation to the total weight of the composition, preferably between 0.3 and 3% in weight.

The compositions according to the invention, preferably for cosmetic or dermatological use, are adapted to a cutaneous topical administration presented under all forms normally used for such an administration. In an advantageous way, they can be under the form of a powder, an emulsion, a microemulsion, a nanoemulsion, a suspension, a lotion, a cream, an aqueous or hydroalcoholic gel, a foam, a serum, a solution or a dispersion for spray, or a dispersion of lipidic vesicles.

They can also be formulated for an administration by oral route (per os administration), under the form for instance of tablets, capsules, capsules, seals, bulbs, syrup, drops.

As examples of physiologically compatible additive with skin, one can mention a compound chosen among oils, waxes, silicone elastomers, surfactants, co-surfactants, thickeners and/or gellants, humectants, emollients, organic filters, inorganic filters, filter boosters and photostabilizing agents, preservatives, dyes, fillers, mothers of pearl, matifying agents, tensors, sequestering agents, perfumes, and their mixtures.

Such examples that can be present in the composition with a content around 0.01 to 20% in relation to the total weight of the composition, are notably mentioned in the "International Cosmetic Ingredient Dictionary and Handbook" dictionary (13rd edition, 2010) published by the "Personnal Care Product Council (PCPC, ex-CTFA)" of the American Cosmetic Association. These examples can be (without this list is limitative): silicone oils, natural or synthetic oils, linear or branched hydrocarbons, synthetic esters and ethers, hydrocarbonated waxes, emulsifying surfactants, linear or branched fatty alcohols, reticulated homo- and copolymers, gums, cellulose derivatives, alginates, polyols, sugars, glycosaminoglycans and other amino acids, mineral or organic fillers, plant proteins, polysaccharides, and their mixtures.

The compositions according to the invention can also comprise additional active ingredients in such a way that the intrinsically attached effect to the compositions according to the invention is not affected by the considered addition, in particular at least an active ingredient chosen among agents that stimulate the production of growth factors, anti-glycation or deglycation agents, agents that increase the synthesis of collagen or prevent its degradation, agents that increase the synthesis of elastin or prevent its degradation, agents that increase the synthesis of glycosaminoglycans or proteoglycans or prevent their degradation, agents that increase the proliferation or the differentiation of keratinocytes, agents that increase the proliferation of fibroblasts, depigmenting, anti-pigmenting or pro-pigmenting agents, antioxidant or anti-radical or anti-pollution agents, agents that stimulate the hydration and/or protect the skin barrier function, agents that increase the synthesis of epidermic lipids, agents that stimulate lipolysis, inhibiting lipogenesis and/or inhibiting adipocyte differentiation, draining or detoxifying agents, anti-inflammatory agents, penetration enhancer agents, desquamative agents, soothing and/or anti-irritating agents, astringent agents, agents that act on the microcirculation, agents that act on the cell metabolism, and their mixtures.

Such examples of additional active ingredients can be present in the composition with a content around 0.001 to about 10% in relation to the total weight of the composition, and can be notably chosen among plant extracts, silicon derivatives, yeast and algae extracts, plant protein hydrolysates, (acylated or not) oligopeptides, coffee extracts, carcinine and its derivatives, carnosine and its derivatives, N-acetylcysteine and its derivatives, hydrosoluble vitamins such as vitamins B1, B2, B3, B6, B12, C, H, liposoluble vitamins such as vitamins A, D2, D3, E and carotene, urea and its derivatives, taurine and its derivatives, polyphenols, oligo- and polysaccharides, lactic, glycolic, citric and salicylic acids and their esters or salts, and their mixtures.

Another object of the invention also concerns the use of a methionine-derived peptidomimetic as a cosmetic agent intended for protecting and/or stimulating the mitochondria of cutaneous cells, said derivative being of the following general formula (III):

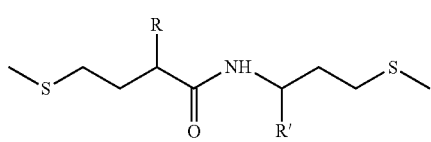

(III)

R=X—C(O)—NH— with X=alkyl or alkyloxy ($C_1$-$C_8$); R'=H or —C(O)R" with R"=Oalkyl ($C_1$-$C_4$), $NH_2$

OR

R'=—C(O)—OX with X=alkyl ($C_1$-$C_8$); R=H

According to a preferred embodiment of the invention, said derivative is of the following general formula (III):

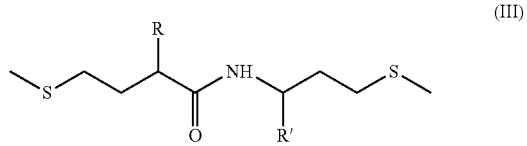

(III)

R=X—C(O)—NH— with X=alkyl or alkyloxy ($C_1$-$C_8$); R'=H or —C(O)R" with R"=Oalkyl ($C_1$-$C_4$), $NH_2$ According to a preferred embodiment of the invention, it is aimed at preventing or fighting against the cutaneous signs of aging with the above-mentioned use of said derivative, preferentially against the cutaneous signs of photo-induced aging, particularly against damages caused to skin by ultra-violet radiations.

A last object of the invention concerns a methionine-derived peptidomimetic for its use in a dermatological composition useful for the treatment of the cutaneous signs of aging, preferentially against damages caused to skin by ultra-violet radiations, said derivative being of the following general formula (III):

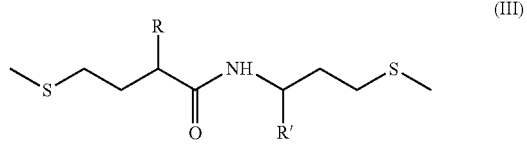

(III)

R=X—C(O)—NH— with X=alkyl or alkyloxy ($C_1$-$C_8$); R'=H or —C(O)R" with R"=Oalkyl ($C_1$-$C_4$), $NH_2$

OR

R'=—C(O)—OX with X=alkyl ($C_1$-$C_8$); R=H

According to a preferred embodiment of the invention, said derivative is of the following general formula (III):

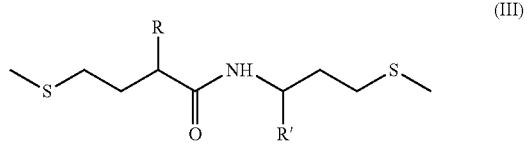

(III)

R=X—C(O)—NH— with X=alkyl or alkyloxy ($C_1$-$C_8$); R'=H or —C(O)R" with R"=Oalkyl ($C_1$-$C_4$), $NH_2$ As non limitative examples of compounds with formula (III), one can especially mention the following compounds:
—N-acetyl-(DL)-methionyl-4-(methylthio)propylamine
—N-propionyl-(DL)-methionyl-4-(methylthio)propylamine
—N-pentanoyl-(DL)-methionyl-4-(methylthio)propylamine
—N-t-butyloxy-(DL)-methionyl-4-(methylthio)propylamine —N-4-(methylthio)-butyryl-L-methionine methylester
—N-acetyl-(DL)-methionyl-L-methionine ethylester In the last both objects of the invention such as above, it is preferentially selected a derivative of general formula (III) such as R is limited to a radical where X is of alkyl-type comprising between one and four carbon atoms ($C_1$-$C_4$) and R' is exclusively a hydrogen atom.

With more preference, it is very particularly selected the N-acetyl-(DL)-methionyl-4-(methylthio)propylamine compound.

EXAMPLE 1

As an illustration, it is hereafter mentioned some formulation examples of composition according to the invention, containing a derivative of the above-mentioned general formula (I):

Formula A (Cream)

| | |
|---|---|
| N-acetyl-(DL)-methionyl-4-(methylthio)propylamine | 1% |
| Hydrogenated polyisobutene | 7% |
| Isobutyl myristate | 3% |
| Cetyl Palmitate | 7% |
| Ethylene glycol monostearate | 5% |
| Sorbitan laurate | 2% |
| Polysorbate 20 | 2% |
| Carbomer (acrylate copolymer/acrylamide & mineral oil) | 0.3% |
| Phenoxyethanol | 0.5% |
| Sodium benzoate | 0.2% |
| Water | qsp 100% |

Formula B (Gel)

| | |
|---|---|
| N-t-butyloxy-(DL)-methionyl-4-(methylthio)propylamine | 3% |
| Carbomer (acrylate copolymer/acrylamide & mineral oil) | 1.5% |
| Sodium benzoate | 0.2% |
| Sorbic acid | 1% |
| 1,3-butanediol | 10% |
| Glycerin | 5% |
| Sodium carbonate | 0.13% |
| Phenoxyethanol | 0.9% |
| Water | qsp 100% |

Formula C (Capsule, Per os Administration)
N-acetyl-(DL)-methionyl-4-(methylthio)propylamine (200 mg powder/capsule)
OR
N-4-(methylthio)-butyryl-L-methionine methylester (200 mg powder/capsule)
Excipients qsp 1 gelatin capsule: microcristalline cellulose, magnesium stearate.

EXAMPLE 2

As purely an indication, the invention is hereafter illustrated by the following tests above-mentioned in the specification of the invention (tests 1 to 6). It is also to note that in vivo studies are in progress and that the first results can also illustrate the use of some methionine-derived peptidomimetics according to the present invention.

Test 1: Evidence of the Ability of the Methionine-derived Peptidomimetics to Restore the Cellular ATP Levels on Cells Exposed to a Stress ($H_2O_2$):

The experimental study has been carried out on a cell line of fibroblasts called V79, and seeded in a 96 well plate at the rate of 5000 cells per well in 100 µl of culture medium (containing 10% foetal calf serum). This one is then replaced in each of the well by 100 µl of medium containing some peptidomimetics according to the invention, at the concentration of 7.5 mM or 10 mM. After 2 hours of incubation, the medium is removed from all wells. Then the cells are submitted to a stress with the addition of a medium containing 50 µl of hydrogen peroxide $H_2O_2$ (4 ppm). After 8 additional hours of incubation, the ATP average concentration is measured by luminometry in presence of luciferin ("ATPlite lstep" kit) and through a standard curve prepared from highly purified ATP.

The results, expressed as the average values obtained from three independent experiments, are presented in the hereafter table 1, in comparison with a control.

TABLE 1

| Compound | ATP ($\times 10^{-7}$M) |
|---|---|
| Control | 4.42 |
| control + $H_2O_2$ | 0.4 |
| N-acetyl-(DL)-methionyl-4-(methylthio)propylamine 7.5 mM | 5.91 |
| N-acetyl-(DL)-methionyl-4-(methylthio)propylamine 7.5 mM + $H_2O_2$ | 4.83 |
| N-propionyl-(DL)-methionyl-4-(methylthio)propylamine 10 mM | 5.28 |
| N-propionyl-(DL)-methionyl-4-(methylthio)propylamine 10 mM + $H_2O_2$ | 4.49 |

The ATP quantity massive drop observed for the control is very greatly prevented in presence of the compounds according to the invention, thus demonstrating their ability to restore the ATP production within cells exposed to a stress.

Test 2: Percutaneous Absorption Study of the Methionine-derived Peptidomimetics on Human Skin Explants:

The values of permeability coefficient (Kp) were obtained from a previously frozen abdominal plastie human skin, in accordance with protocol described in the OECD guidelines n° 428 on cutaneous absorption studies.

Experimentally, the skin explants were placed on Frantz-type cells in passive diffusion, piloted by the "MicroettePlus Hanson Research" system. The tested products are applied in a non-occlusive way. After that skin was laid on the cells, 500 µl of peptidomimetic according to the invention (1% solution) were placed in each of the cells and for a total contact time of 24 hours. At the end of these ones, the remaining product is sampled and the skin surface rinsed for extraction and for measure of the absorbed quantity, then for the determination of the permeability coefficient expressed under logarithmic type (Log Kp).

The results are gathered in the hereafter table 2.

TABLE 2

| Compound | Kp (cm · $h^{-1}$) | Log Kp |
|---|---|---|
| caffeine | $1 \cdot 10^{-4}$** | −4.0 |
| N-acetyl-(DL)-methionyl-4-(methylthio)propylamine | $1.09 \cdot 10^{-4}$ | −3.96 |
| N-propionyl-(DL)-methionyl-4-(methylthio)propylamine | $9.7 \cdot 10^{-5}$ | −4.0 |
| N-pentanoyl-(DL)-methionyl-4-(methylthio)propylamine | $3.7 \cdot 10^{-4}$*** | −3.43 |
| N-t-butyloxy-(DL)-methionyl-4-(methylthio)propylamine | $4.6 \cdot 10^{-4}$*** | −3.34 |
| N-4-(methylthio)-butyryl-L-methionine methylester | $2 \cdot 10^{-4}$*** | −3.71 |
| N-acetyl-(DL)-methionyl-methionine ethylester | $1.64 \cdot 10^{-4}$*** | −3.78 |

**Mitragotri S., J. Controlled Release, (2003), vol.86, pp.69-92
***according to predictive software "ChemDraw ultra version 11.0", supplier: Cambridge-Soft Ltd The permeability coefficient obtained for the compounds according to the invention is similar to that one obtained for the recognized trans-stratum corneum permeant, caffeine.

Test 3: Evidence of the Protective Effect of the N-Acety-(DL)-Methionyl-4-(Methylthio)Propylamine Compound on the Mitochondrial Oxidative Stress and on the Mitochondrial Biogenesis Principles: measures of the mitochondrial intracellular oxidative stress and detection of the mitochondrial biogenesis were achieved by flux cytometry with the following fluorophore markers:
- the "MitoSOX™ Red" red fluorescent probe below-designed "MitoSOX" (detection to λ=580 nm; supplier: Invitrogen) allows to specifically detect the $O_2^{\circ-}$ superoxide anion present in mitochondria (due to its strong affinity for mitochondria),
- the "MitoTracker® Green FM" green fluorescent probe below-designed "Mitogreen" (detection to λ=516 nm; supplier: Invitrogen) allows to quantify the mitochondrial mass (or related number of mitochondria per cell).

Experimentally, tests were achieved on a fibroblastic line of hamster "V79", maintained by lining out in a "EMEM" complete culture medium (with 10% foetal calf serum) in humid atmosphere at 37° C. and 5% $CO_2$. The V79 cells are seeded then incubated 24 hours in 96 well plates at the rate of $2.5 \cdot 10^5$ cells per well in 3 ml of the same culture medium, then exposed 1h30 to a stress with the addition of a medium containing hydrogen peroxide $H_2O_2$ (15 ppm).

After trypsination, the cells are incubated at 37° C. for 15 minutes in 1 ml of "EMEM" complete culture medium and containing the above-mentioned markers "MitoSOX" (at the final concentration of 5 μM) and "Mitogreen" (at the final concentration of 200 nM), for respective detection:
- of the mitochondrial oxidative stress (expressed in % of positive cells)
- of the mitochondrial mass per cell (expressed in % of MFI ("Mean Fluorescence Intensity") in relation to the control).

The results, expressed as the average values obtained from four independent experiments, are presented in the hereafter tables 3a and 3b, in comparison with those obtained for the N-acetyl-cysteine chosen as a reference protective agent at the concentration of 5 mM.

TABLE 3a

|  | % of positive cells to MitoSOX |
|---|---|
| control | 18 |
| control + $H_2O_2$ | 85.7 |
| N-acetyl-cysteine 5 ppm + $H_2O_2$ | 15.2 |
| N-acetyl-(DL)-methionyl-4-(methylthio)propylamine 7.5 mM + $H_2O_2$ | 40.3 |

TABLE 3b

|  | MFI (% control) |
|---|---|
| control | 100 |
| control + $H_2O_2$ | 177.3 |
| N-acetyl-cysteine 5 ppm + $H_2O_2$ | 74.4 |
| N-acetyl-(DL)-methionyl-4-(methylthio)propylamine 7.5 mM + $H_2O_2$ | 123.5 |
| N-acetyl-(DL)-methionyl-4-(methylthio)propylamine 10 mM + $H_2O_2$ | 127.5 |

In both cases, the results highlight for the N-acety-(DL)-methionyl-4-(methylthio)propylamine compound an ability to reduce the effect of intramitochondrial stress.

Test 4: Evidence of the Cytoprotective Effect of the N-Acety-(DL)-Methionyl-4-(Methylthio)Propylamine and N-t-Butyloxy-(DL)-Methionyl-4-(Methylthio)Propylamine:

The experimental study was carried out on a fibroblastic line of hamster "V79", maintained in humid atmosphere at 37° C. and 5% $CO_2$, then seeded in 96 well plates at the rate of $0.5 \cdot 10^4$ cells per well in 0.2 ml of "EMEM" culture medium (with 10% foetal calf serum). The cells are then exposed 24 hours to a state of toxic stress, with the replacement of the culture medium by a medium containing hydrogen peroxide $H_2O_2$ (4 ppm), medium to which is simultaneously added the compound according to the invention.

After removal of the medium, the cell viability of fibroblasts is measured via the "MTT method" or bromide of 3-(4,5-dimethylthiazol-2-yl)-2,5-diphenyltetrazolium (solution at 500 μl/ml) and by spectrophotometry (absorbance at 540 nm).

The results, expressed as the average values obtained from three independent experiments, are presented in the hereafter table 4, again in comparison with those obtained for the N-acetyl-cysteine at 5 mM chosen as a reference cytoprotective agent (total restoration of cell viability).

TABLE 4

|  | % cell viability |
|---|---|
| control | 100 |
| control + $H_2O_2$ | 54.8 |
| N-acetyl-cysteine 5 mM + $H_2O_2$ | 103.8 |
| N-acetyl-(DL)-methionyl-4-(methylthio)propylamine 7.5 mM + $H_2O_2$ | 83.5 |
| N-acetyl-(DL)-methionyl-4-(methylthio)propylamine 10 mM + $H_2O_2$ | 91.9 |
| N-t-butyloxy-(DL)-methionyl-4-(methylthio) propylamine 7.5 mM + $H_2O_2$ | 70.1 |
| N-t-butyloxy-(DL)-methionyl-4-(methylthio) propylamine 10 mM + $H_2O_2$ | 77.3 |

The results of the table 4 highlight a dose-dependent cell viability and an ability to protect the cells from a cytotoxic stress for the compounds according to the invention.

Test 5: Evidence of the Antioxidant Effect of the N-Acety-(DL)-Methionyl-4-(Methylthio)Propylamine and N-Propionyl-(DL)-Methionyl-4-(Methylthio)Propylamine on the Hydroxyl Radical The method, described by Rehman A. and coll. (British J. Pharmacol. (1997), vol. 122, pp. 1702-1706), is used for the determination of the scavenging speed constant of the hydroxyl radical [Ks (OH°)], the peptidomimetic according to the invention being compared to two reference antioxidants, mannitol and ascorbic acid (vitamin C).

Experimentally, the tested substance is dissolved in a buffered medium of pH 7.4 to which is added a OH° generating system (ascorbate/iron/EDTA) in presence of deoxyribose. After one hour of incubation at 37° C., the reaction is stopped with the help of trichloroacetic acid. After colorimetric visualization with thiobarbituric acid, the absorbance is measured at 532 nm for different concentrations, then the relative Ks (OH°) is calculated for each of the substances. The results are reported below in the table 5.

TABLE 5

| Compound | Ks(OH°) ($10^9 \cdot M^{-1} \cdot s^{-1}$) |
|---|---|
| ascorbic acid | 10.1** |
| mannitol | 1.6/1.9*** |
| N-acetyl-(DL)-methionyl-4-(methylthio)propylamine | 6.1 |

TABLE 5-continued

| Compound | Ks(OH°)<br>($10^9 \cdot M^{-1} \cdot s^{-1}$) |
|---|---|
| N-propionyl-(DL)-methionyl-4-(methylthio)propylamine | 5.7 |

**Cabelli D. E., J. Phys. Chem. (1983), vol.87, pp.1809-1812
***Rehman A., British J. Pharmacol. (1997), vol.122, pp.1702-1706

The results, expressed as the average values obtained from three independent experimentations, highlight for the peptidomimetics according to the invention an ability to scavenge the hydroxyl radical (OH) which is much more efficient in comparison with that one for mannitol, and mildly in comparison with that one for ascorbic acid.

Test 6: Evidence of the Antioxidant Effect of the N-Acety-(DL)-Methionyl-4-(Methylthio)Propylamine Compound on Peroxynitrite Ions The method so-called "whitening test of the pyrogallol red (PR)", described by Nath V. B. and coll. (BBRC (2001), vol. 285, pp. 262-266), is used for the determination of the oxidation inhibition of the pyrogallol red (PR) by peroxynitrite ions (ONOO⁻), the N-acety-(DL)-methionyl-4-(methylthio) propylamine compound according to the invention being compared to a reference antioxidant, namely the "Trolox" or carboxylic 2-(6-hydroxy-2,5,7,8-tetramethylchromane) acid which is a hydrosoluble equivalent of vitamin E.

Experimentally in a 96 well plate, 50 μM of PR and 25 μM of peroxynitrite ions ONOO⁻ (in solution in NaOH 0.1 M) are added to the tested substance dissolved in a buffered medium of pH 7.0. After 5 minutes, the absorbance is measured by spectrophotometry at 540 nm, then calculated the $IC_{50}$ (50% inhibitory concentration) related to each of the substances. The results are reported below in the table 6.

TABLE 6

| Compound | $IC_{50}$ (mM) |
|---|---|
| Trolox | 0.083 |
| N-acetyl-(DL)-methionyl-4-(methylthio)propylamine | 1.012 |

Less active than the reference antioxidant, the inhibition of PR oxidation by peroxynitrite ions however remains clearly observed for the compound according to the invention.

The invention claimed is:

1. Methionine-derived peptidomimetic, which is represented by the following general formula (II):

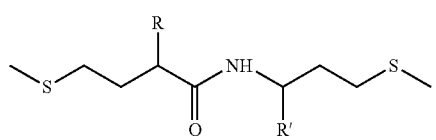

(II)

R=X—C(O)—NH— with X=alkyl or alkyloxy ($C_1$-$C_4$);
R'=H.

2. Peptidomimetic according to claim 1, which is the N-acetyl-(DL)-methionyl-4-(methylthio)propylamine.

3. Composition for use against the cutaneous disorders associated to a mitochondrial dysfunction, which comprises a methionine-derived peptidomimetic of general formula (II):

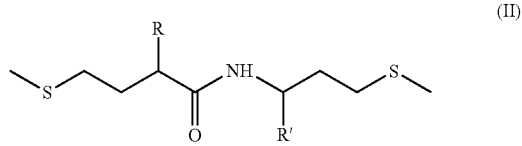

(II)

R=X—C(O)—NH— with X=alkyl or alkyloxy ($C_1$-$C_4$);
R'=H and a physiologically compatible additive.

4. Composition according to claim 3, wherein said peptidomimetic is the N-acetyl-(DL)-methionyl-4-(methylthio) propylamine.

5. Composition according to claim 3, wherein the quantity of said peptidomimetic is comprised between 0.1 and 10% in weight in relation to the total weight of the composition.

6. Composition according to claim 3, which is adapted to a cutaneous topical administration, under the form of a powder, an emulsion, a microemulsion, a nanoemulsion, a suspension, a lotion, a cream, an aqueous or hydroalcoholic gel, a foam, a serum, a solution or a dispersion for spray, or a dispersion of lipidic vesicles.

7. Composition according to claim 3, which it comprises at least one additional active ingredient chosen among agents that stimulate the production of growth factors, anti-glycation or deglycation agents, agents that increase the synthesis of collagen or prevent its degradation, agents that increase the synthesis of elastin or prevent its degradation, agents that increase the synthesis of glycosaminoglycans or proteoglycans or prevent their degradation, agents that increase the proliferation or the differentiation of keratinocytes, agents that increase the proliferation of fibroblasts, depigmenting, anti-pigmenting or pro-pigmenting agents, antioxidant or anti-radical or anti-pollution agents, agents that stimulate the hydration and/or protect the skin barrier function, agents that increase the synthesis of epidermic lipids, agents that stimulate lipolysis, inhibiting lipogenesis and/or inhibiting adipocyte differentiation, draining or detoxifying agents, anti-inflammatory agents, penetration enhancer agents, desquamative agents, soothing and/or anti-irritating agents, astringent agents, agents that act on the microcirculation, agents that act on the cell metabolism, and their mixtures.

8. Composition according to claim 3, which is intended for protecting the skin from a "UV-induced" stress.

* * * * *